(12) United States Patent
Lin et al.

(10) Patent No.: US 10,614,573 B2
(45) Date of Patent: Apr. 7, 2020

(54) METHOD FOR AUTOMATICALLY RECOGNIZING LIVER TUMOR TYPES IN ULTRASOUND IMAGES

(71) Applicant: SUN YAT-SEN UNIVERSITY, Guangzhou, Guangdong (CN)

(72) Inventors: Liang Lin, Guangdong (CN); Qingxing Cao, Guangdong (CN); Qing Wang, Guangdong (CN); Bo Jiang, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 127 days.

(21) Appl. No.: 15/989,457

(22) Filed: May 25, 2018

(65) Prior Publication Data
US 2018/0276821 A1    Sep. 27, 2018

Related U.S. Application Data

(63) Continuation of application No. PCT/CN2016/074645, filed on Feb. 26, 2016.

(30) Foreign Application Priority Data

Dec. 3, 2015  (CN) .......................... 2015 1 0885104

(51) Int. Cl.
| G06K 9/00 | (2006.01) |
| G06T 7/00 | (2017.01) |
| G06K 9/32 | (2006.01) |
| G06T 7/62 | (2017.01) |
| G06T 7/70 | (2017.01) |
| A61B 8/08 | (2006.01) |
| A61B 8/00 | (2006.01) |
| G06K 9/34 | (2006.01) |
| G06K 9/46 | (2006.01) |
| G06K 9/62 | (2006.01) |

(52) U.S. Cl.
CPC ............ *G06T 7/0014* (2013.01); *A61B 8/085* (2013.01); *A61B 8/469* (2013.01); *A61B 8/5223* (2013.01); *G06K 9/3233* (2013.01); *G06K 9/3241* (2013.01); *G06K 9/346* (2013.01); *G06K 9/4604* (2013.01); *G06K 9/4671* (2013.01); *G06K 9/6227* (2013.01); *G06K 9/6257* (2013.01); *G06K 9/6276* (2013.01); *G06K 9/6289* (2013.01); *G06T 7/0016* (2013.01); *G06T 7/62* (2017.01); *G06T 7/70* (2017.01); *A61B 8/481* (2013.01); *G06K 2209/05* (2013.01); *G06T 2207/10132* (2013.01); *G06T 2207/20072* (2013.01); *G06T 2207/20076* (2013.01); *G06T 2207/20081* (2013.01); *G06T 2207/30056* (2013.01); *G06T 2207/30096* (2013.01)

(58) Field of Classification Search
CPC .................................................... G06T 7/0014
USPC ....................................................... 382/128
See application file for complete search history.

*Primary Examiner* — Stephen P Coleman

(57) ABSTRACT

The disclosure relates to a method for automatically recognizing liver tumor types in ultrasound images. The method specifically comprises: using a plurality of Regions of Interest (ROIs) to represent a CEUS image; different lesions are distinguished by the performance and changes of the ROI in time and space; representing a space-time relationship between ROIs by establishing a model in time and space at the same time; and determining, by the model, a relatively appropriate ROI and relevant parameters of the model according to existing CEUS lesion samples by means of an iterative learning method. After giving a sample, an appropriate ROI can be determined and a reference diagnosis for the lesion can be given by removing part of inappropriate ROIs in advance and by means of a rapid search method.

5 Claims, 3 Drawing Sheets

METHOD FOR AUTOMATICALLY RECOGNIZING LIVER TUMOR TYPES IN ULTRASOUND IMAGES

CROSS REFERENCE TO RELATED APPLICATIONS

The present application is a Continuation Application of PCT Application No. PCT/CN2016/074645 filed on Feb. 26, 2016, which claims the benefit of Chinese Patent Application No. 201510885104.X filed on Dec. 3, 2015. All the above are hereby incorporated by reference.

TECHNICAL FIELD

The disclosure relates to the field of medical image processing and, in particular, to a method for automatically recognizing liver tumor types in ultrasound images.

BACKGROUND

Liver tumors are the fifth most common tumors and the second leading cause of death in cancer. Focal Liver Lesions (FLLs) are abnormal solid or cystic masses in the liver. The discovery of FLLs in the early stage of liver cancer and the diagnosis of FLLs may have important significance for the treatment of liver cancer. In the process of diagnosis, medical images have played a very important role, and especially in recent years, with the development of an imaging technology, the location of medical images in diagnosis is more and more important. Medical images comprise Computerized Tomography (CT), Magnetic Resonance Imaging (MRI), and Ultrasound (US) imaging, among which the CT and the MRI require high costs and complex instruments, and the CT may also cause ionizing radiation. The US imaging has become more and more widely used because of its low price, fast imaging, and noninvasive imaging. However, due to an imaging mechanism of ultrasound, images obtained by the US imaging are blurred, have a low resolution, and have a low signal-to-noise ratio. The recently proposed Contrast-Enhanced Ultrasound (CEUS) imaging method studies a dynamic enhancement pattern of FLLs over a period of time by continuously imaging FLLs over a period of time. By studying the differences and changes of an FLL region with respect to surrounding healthy tissues over time, CEUS can significantly improve the detection results of FLLs. The use of CEUS images for assisted diagnosis not only helps doctors to obtain more information and improves the efficiency of diagnosis, but also reduces unnecessary pain for patients.

During the actual diagnosis of liver tumors using CEUS images, a doctor usually injects a contrast agent into the blood vessels of a patient. As the contrast agent flows along with blood in the body, the CEUS images will form four main phases namely a plain phase, an arterial phase, a portal phase, and a delayed phase. The duration and imaging features of each region are different. A radiologist identifies the FLLs, typically by observing an enhanced change form of a lesion region over the three phases (arterial phase, portal phase, and delayed phase). The portal and delayed phases are mainly used to distinguish between malignant cancers, such as Hepatocellular Carcinoma (HCC), and benign cancers, such as Hemangiomas (HEM) and Focal Nodular Hyperplasia (FNH). Most of the malignant cancers show a low enhancement in portal and delayed phases while most of the benign cancers show flat enhancement or high enhancement. On the other hand, the arterial phase may provide useful information for distinguishing specific liver cancer categories. For example, the vast majority of HCC cases are highly enhanced in the arterial phase, while some cases are not uniformly enhanced or show a circular enhancement around a larger nodule. In benign cases, most of HEM cases show a peripheral nodular increase, another part shows a rapid and uniform high enhancement. FNH cases may show a spoke-like enhancement or a uniform high enhancement in the arterial phase. Different changes in these same cases described above will also be considered at the time of diagnosis.

At this stage, the accuracy of diagnosis depends heavily on the experience and level of a diagnosis doctor. At the time of diagnosis, doctors often need to repeatedly view the entire section of CEUS image, find the location of the lesions in the images and an imaging mode of the lesions, and finally diagnose the cases according to their own medical knowledge or medical knowledge in literatures. The diverse and complex enhancement pattern of the liver cancer mentioned above also brings great difficulties in distinguishing different FLL types. In addition, the CEUS imaging is ambiguous and requires experienced doctors to perform detailed observations to identify and diagnose. This usually takes a lot of time to deal with every case. At the same time, the length of a section of CEUS image is usually 3 to 5 minutes. When the number and data of patients increase, it will undoubtedly require a lot of labor and time for the doctor.

On the other hand, the field of computer vision has developed rapidly in recent years, and many good results have been achieved in the field of natural images and imaging such as object recognition, positioning, detection, scene classification, segmentation, video tracking, motion recognition and even semantic analysis. With the rapid development of the field of machine learning, the combination of computer vision and machine learning is becoming more and more intimate. Computer vision has begun to not only simply process images and video itself, but has begun to understand and process the content and even semantics of images and videos. On some data sets, the accuracy of the method for detecting objects has even exceeded the human itself. The data and structure of medical images in computers are not essentially different from natural images. Information about a pixel is represented by a single value. Therefore, methods and technologies in computer vision may be transformed into the field of medical images. The method of analyzing image and video content in computer vision may also be practiced and applied in the field of medical images. If the analysis and understanding of a medical image can be realized, the computer may be used to assist a doctor in aided diagnosis. By giving the key part and the key time in the image, the imaging and changing features in an image will be given, which may save plenty of time for the doctor's diagnosis. For new physicians, Computer-Aided Diagnosis (CAD) systems can help or guide them in identifying lesions, which is an important aid to training experienced doctors. So in reality, the analysis of medical images has a very considerable application prospect and value.

As mentioned above, with the development of computer technologies such as a medical image processing technology, machine learning, pattern recognition and a computer vision technology, CAD systems have also been developed and applied. In many other medical fields such as breast cancer, CAD systems have achieved good results by assisting physicians in the analysis and interpretation of medical images. At present, the relatively mature technologies of CAD systems for medical images comprise de-noising, segmentation, registration, 3D reconstruction, and so on.

De-noising comprises: preprocessing an image, such as adjusting a contrast and sharpening the image, so that imaging is more conducive to the doctor's observation; the segmentation is to separate the same organ or region in an image or image sequence from other parts, and prepare for the next step of the CAD system; the registration is to match the same part of different types of medical images in the same case, thereby making it easier for doctors to view the same region in different medical images; imaging of some techniques such as CT is to scan a part of a human body layer by layer to form a two-dimensional tomographic image; and the 3D reconstruction is to combine these two-dimensional images to form a three-dimensional model of an organ or region.

Although a current CAD system has a certain degree of application in these aspects, most of them are dealing with medical images. The existing systems mainly focus on segmentation of tissues and organs, interactive and automatic segmentation of focal lesions, edge detection and so on. The medical image processing is also mostly concentrated on images such as CT that are clearly imaged and easy to handle. In the FLL recognition and diagnosis part of a CEUS image, because of the disturbance of a lesion region in three imaging stages of the CEUS image and various imaging patterns, few CAD systems can analyze and recognize FLLs in the CEUS image. Even some of the cutting-edge methods rely on manually determining the locations and regions of the FLLs. The accuracy of manual annotation is highly related to the doctor's technical and domain knowledge. Different doctors also have different understandings of the lesions, which may cause the annotation time and location to be slightly different. On the other hand, with the increase in acquisition and processing technologies, the number of CEUS data is growing at a fairly high rate. Manual annotation requires a lot of time for doctors. Therefore, a fully automated CAD system for analyzing and diagnosing FLLs is extremely necessary.

In the field of medical image processing, there is not much work to recognize liver FLLs in CEUS images. Some methods use a quadratic curve to fit the average grayscale temporal changes in the lesion region to represent an imaging pattern of lesions in CEUS imaging to distinguish the lesion type and separate FNH from other lesion types; or the lesion region is manually segmented, and multiple cascaded neural networks are used to classify lesions. There is also a method to propose a Dynamic Vascular Pattern (DVP) to represent the imaging features of the lesions. During the test, the surrounding normal tissue and lesion regions are manually marked in a certain frame, an average grayscale curve of two parts in the entire image can be automatically generated, and then this curve is used to distinguish between benign and malignant tumors, thereby achieving a very good effect. In the above work, more or less interactions are needed to determine the location of lesions or normal tissues manually. Human interaction relies heavily on the knowledge, skills and experience of an operator, and it is easy to make different doctors have different interpretations of the same case, thereby causing disturbances in results. On the other hand, with the continuous growth of ultrasound image data, if doctors need to manually interact with each case, they will consume a lot of energy and time, and manual annotation of all data will become more and more difficult. Therefore, a system that can automatically perform aided diagnosis without manual interaction is necessary.

In another field of medical image processing, it focuses on automatic detection or segmentation of other types of tumors. By using grayscale information, these methods can find edge and region features, and ultimately achieves segmentation of multiple tumors in a variety of medical images.

Another type of treatment for liver tumors in ultrasound images is to track liver tumors in consecutive CEUS images. Due to human respiration and motion, jitter of an operator and the like, the tumors in the ultrasound images will often change locations and sizes, and sometimes they will be blocked, causing the grayscale of the tumors to change or even disappear. Most of the methods in this field perform tracking by region matching via various features or slight disturbances. Or, a spatial relationship between local information of a region and the region is considered at the same time, and a model is used to jointly express the two. To prevent tracking errors from accumulating over time, some methods also use models to express a relationship between image appearance information and tumor bias. It starts with human respiration and tries to correct the offset locations of the tumors by performing template matching on the tissues in some frames, or by finding out the errors caused by human respiration, and finally, the tracking accuracy is improved. Determining the location of the lesion is a very important step in the recognition of this method, but these methods still do not recognize the FLLs. The field of medicine still does not directly recognize the types of lesions.

SUMMARY

An objective of the disclosure is to overcome the defects in the related art, to make up for the gaps in the related art, and to provide a method for automatically recognizing liver tumor types in ultrasound images.

To achieve the objective of the disclosure, the disclosure adopts the technical solution as follows.

A method for automatically recognizing liver tumor types in ultrasound images comprises the steps as follows.

In S1, a model is used to represent a case, and a local classifier is used to represent possible change forms of a lesion.

In S2, ultrasound images of a group of cases and the type of liver cancer in each case are input as a training sample.

In S3, the values of model parameters are all initialized to 0, or are randomly initialized with a Gaussian probability distribution which has the expectation of zero.

In S4, based on the model parameters, in an ultrasound image video of a case, a dynamic programming algorithm is used to search for an optimal Region of Interest (ROI) location, size, and time for each local classifier, so that when a model determines that the lesion class of the training sample is correct, a maximum score is obtained.

In S5, a graph cut algorithm is used to determine a specific change form and ROI of the case.

In S6, based on the ROI determined in S5, the training sample in S2 is used as an input, a cutting-plane algorithm is used to train it, and outputs of the algorithm are used as model parameters to obtain possible locations and sizes of lesions in the case and the number of local classifiers.

In S7, S4 to S6 are repeated to acquire the lesion type of each case of a training sample data type, the correctness of the acquired lesion type is judged, and when the number of judgment errors is fixed or the number of repetition steps reaches a preset value, training model parameters are obtained.

In S8, the training model parameters acquired in S7 are used to determine an optimal ROI location, size, and time for all local classifiers in an ultrasound image video of a case to be detected; a graph cut algorithm is used to determine a specific change form and ROI of the case to be detected; and a model is used to obtain a probability score for a lesion according to the determined change form and ROI.

In S9, S2 to S8 are repeated for all lesion types in the case to be detected, and a probability score for one lesion is obtained by each repetition, a lesion type corresponding to the highest probability score being the lesion type of the case to be detected.

Preferably, an ROI is respectively extracted for an input case ultrasound image at three phases namely an arterial phase, a portal phase and a delayed phase, the three ROIs being used to express FLLs.

Appearance features of an ROI interior, appearance features of an ROI boundary and appearance features of an ROI periphery are respectively extracted on the ROI interior, the ROI boundary and the ROI periphery of the ROI at each phase, and an average grayscale difference between the ROI interior and the ROI boundary and an average grayscale difference between the ROI interior and the ROI periphery are also acquired in the ROI at each phase.

When regional features of the ROI interior, the ROI boundary and the ROI periphery are extracted, the contrast, correlation, energy, and identity of a regional grayscale co-occurrence matrix are used as appearance features.

The ROI interior is obtained by reducing the selected ROI, and the ROI periphery is obtained by amplifying the selected ROI.

The local classifier is a linear local classifier, the local classifier being used to determine the FLL change class of an ROI at a certain phase.

Preferably, model parameters in S2 are all initialized to 0, or are randomly initialized with zero expectation.

Preferably, in S3, pruning is used first, and then an optimal ROI is searched by using a dynamic programming method. A specific process is as follows.

A pruning process comprises time and space pruning.

The time pruning is: calculating the grayscale feature of a grayscale co-occurrence focus in a certain frame in an ultrasound image video, and making a difference between vector frames to obtain a change value used to represent each frame; using a series of values obtained within a period of time to represent the degree of change of each frame within the period of time; arranging this series of values in a time sequence, and extracting the local maximum points to obtain a frame most dramatically changing within a period of time; selecting these frames corresponding to the local maximum points to obtain candidate frames of a lesion region; and in the remaining candidate frames, removing some unimportant regions based on experience.

The space pruning is mainly achieved by using a priori of significance and location, comprising: calculating a saliency map of the entire image first, normalizing the saliency map, and averaging salient values in a region to obtain a salient value of the region, the priori of location being image-centered Gaussian distributions; and multiplying the values obtained from priori information of these two parts to obtain the probability that a certain region is an FLL region, and selecting a region of the probability is greater than the threshold as a candidate ROI.

Dynamic programming is used to search an ROI; after time and space pruning, a different number of frames will be retained within three different phases, and a different number of candidate ROIs will be retained within each frame; and in the timing constraint, two ROIs adjacent to each other in a chronological order must be close to each other at a spatial location. The dynamic programming method is: finding an ROI within a previous phase, so that it is in the vicinity of a current ROI, and its score plus timing relationship score of the current ROI can reach a maximum value; then searching a local classifier, so that an appearance score of the current ROI is maximized.

Preferably, in S3, after searching for an optimal ROI, selection of the local classifier for the case will also be adjusted. The adjustment mode is: increasing, decreasing, or maintaining the number of local classifiers.

In this process, the goal is to maximize a local classifier score selected for each case while maximizing the similarity measure of two cases' ROIs under the same local classifier.

Preferably, a specific mode to achieve the above goal is: using a Euclidean distance between two ROI features as a measurement of similarity, and using a graph cut algorithm to solve the problem by converting into a graph label problem.

Compared with the related art, the beneficial effects of the disclosure are as follows. The method for automatically recognizing liver tumor types in ultrasound images provided by the disclosure can rapidly and accurately obtain the lesion type of a case and overcome the shortage of manually determining a lesion region.

DETAILED DESCRIPTION OF THE EMBODIMENTS

The disclosure will be further described below with reference to the drawings, but the embodiments of the disclosure are not limited thereto.

The disclosure mainly provides a method for automatically recognizing liver tumor types in ultrasound images, comprising two parts: a method for representing a liver tumor in an ultrasound image; and a method for automatically determining the location, time and size of a lesion in an ultrasound image and recognizing the lesion.

For the convenience of description, key terms are defined as follows.

"Vector" is a set of sequentially arranged numbers that can be represented in a computer programming language, such as an array in C language.

"Model" is a set of rules that can take a video of a case as an input and output it as a possible value for a particular lesion. In this method, the model divides the input into a vector with a certain structure according to the rules, and multiplies model parameter vectors by elements to obtain a possible value. The larger the value is, the more likely it belongs to that type of lesion.

"Model parameter" is a vector. By inputting ultrasound image videos of multiple cases and corresponding lesion types by a user, a specific value of a model vector may be obtained by using a learning method in the disclosure.

"ROI" is a region on a video frame that consists of all pixels in this portion of a frame of image. In this method, these regions are identified as lesion regions.

"Local classifier" is a part of the model. An ROI is input, and a value indicating whether the ROI belongs to a specific change form of a certain lesion. The larger the value is, the more likely it belongs to that specific change.

Figure 1:
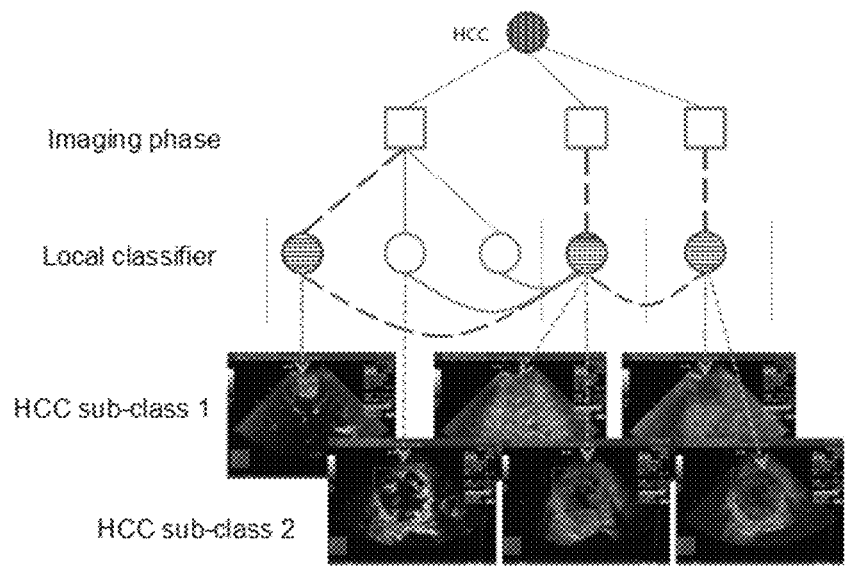
FIG. 1 is a diagram of a space-time AND-OR model.

For an ultrasound video of a case, this method comprises: automatically extracting an ROI in a certain frame at three imaging phases as the location of a lesion, and representing it with an AND-OR model structure. The model structure is as shown in FIG. 1. The three imaging phases in FIG. 1 are combined to represent a case class.

An imaging mechanism of ultrasound images makes each ROI change considerably at different times and in different cases. At the same time, internal echo and posterior echo enhancements will be generated in the ultrasound image, thereby making it more important to refer to an enhancement pattern of surrounding tissues when extracting the features of the ROI.

This method extracts the features of the ROI in the following ranges: an ROI interior, used to describe a lesion itself; an ROI boundary, used to describe the shape of the lesion; and a normal tissue portion within a certain range of an ROI periphery, used to describe a posterior echo enhancement pattern of this ultrasound image. In addition, an internal echo pattern of the lesion is obtained by making a difference between an average grayscale of a lesion region and surrounding and an average grayscale of a lesion region edge and a lesion interior.

When extracting the features of the three regions of the ROI, the contrast, correlation, energy, and identity of a region grayscale co-occurrence matrix are used as appearance features in this method. Thus, a feature vector of the ROI is represented by five parts: appearance features of an ROI interior, appearance features of an ROI boundary, appearance features of an ROI periphery, an average grayscale difference between the ROI interior and the ROI boundary, and an average grayscale difference between the ROI interior and the ROI periphery.

The other features of the case consist of a vector obtained by making a difference between appearance feature vectors of two ROIs and a Euclidean distance from spatial coordinates of the two regions. This part correspondingly represents timing features of the case.

Figure 2:
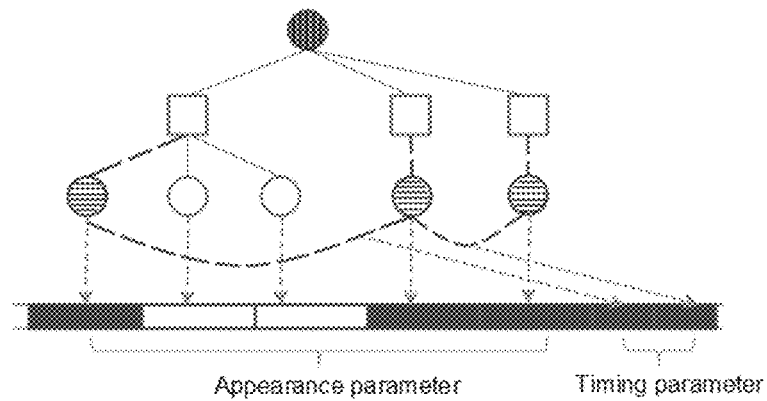
FIG. 2 is a diagram of model parameters.

All the appearance features and the timing features are spliced together to obtain a representation mode as shown in FIG. 2, where a circle with horizontal lines represents a selected local classifier, and a hollow circle represents an unselected local classifier, corresponding features being set as 0.

The above method may convert a piece of ultrasound image video into features, represented by a vector. This vector will be used for ultrasound image recognition.

After obtaining the vector representation of the ultrasound image, the following steps are needed to recognize a liver cancer lesion region in the ultrasound image.

1. A user inputs ultrasound images of a group of cases and the type of liver cancer in each case as training data.
2. An initial value is set for a model parameter.
3. The model parameter is used to determine an optimal ROI location, size and time for all local classifiers in an ultrasound image video of each case.
4. A graph cut algorithm is used to determine a specific change form and ROI of each case.
5. The model parameter is trained by using an SVM method based on these ROIs.
6. S3 to S5 are repeated; until the lesion type of the training data is judged, it is determined that the number of judgment errors is no longer reduced; or until the number of repetition steps reaches a preset value, a model parameter is obtained.
7. A case is given, and the model parameter and method obtained above are used to obtain the ROI location, size, time and change pattern of the case.
8. The above steps are repeated for all possible lesion types, the most likely type being a lesion type recognized by this method.

Herein, model parameters in S2 may be all initialized to 0, or randomly initialized with zero expectation.

In S3 to S5, a Latent Structural SVM method is used to optimize a model. While obtaining the model parameters, the possible location and size of a lesion and number of local classifiers in the training data are determined. Iterative training is performed between an objective function of the optimized model and the determined ROI.

In S3, the method searches for the size, location and frame of an ROI with the highest score for each local classifier when calculating a hidden variable via a fixed model parameter. During searching for the ROI, this method uses pruning first and then uses dynamic programming.

In an ultrasound image, two frames generally appear to be very smooth, and when a lesion region starts to show an enhancement pattern, the grayscale will generally have a large change with the nearby frame in a time sequence. Therefore, in some periods of time, when a lesion region enhancement pattern is obvious, those frames that have the greatest change in grayscale are more likely to be selected to be used as temporal candidate frames.

Specifically speaking, for a certain frame in the ultrasound image, grayscale features of a grayscale co-occurrence focus are calculated on this frame, and a difference is made between vector frames to obtain a value used to represent the degree of change of each frame. By arranging this string of values in a chronological order and extracting the local maximum points from it, a frame most dramatically changing within a period of time may be obtained. By selecting these frames, candidate frames of the lesion region may be obtained.

Figure 3:
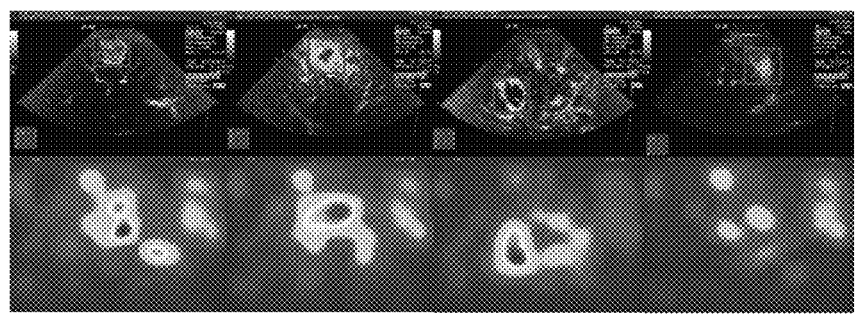
FIG. 3 is a diagram of space pruning.

After the time pruning in the previous step, less important regions are removed in the remaining candidate frames. In this step of pruning, the significance and location priori are mainly used. First, the saliency map of the entire image is calculated, and normalized, and the salient values in the region are averaged to obtain a salient value of the region. The second location priori is image-centered Gaussian distribution. The values obtained from the priori information of these two parts are multiplied to obtain the probability that a certain region is an FLL region, as shown in FIG. 3. A threshold is set, and a region having a probability greater than the threshold is selected as a candidate ROI, where a circle shown in FIG. 4 is a candidate ROI.

Figure 4:
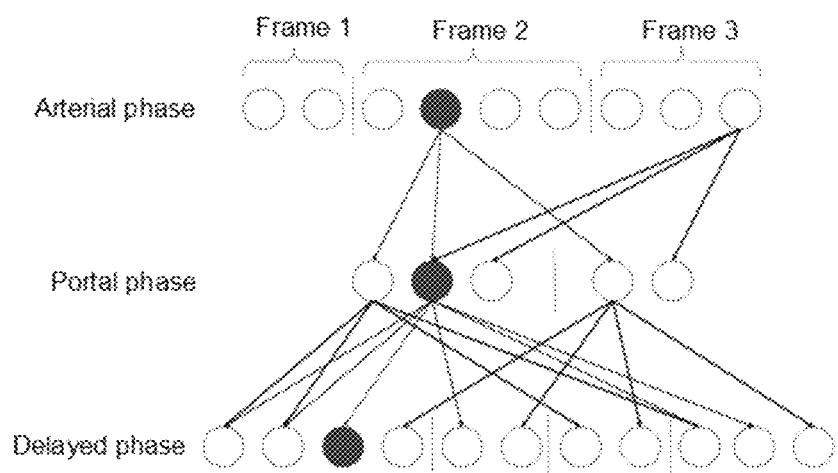
FIG. 4 is a diagram of dynamic programming reasoning in a model reasoning method.

Dynamic programming is then used to search an ROI; after time and space pruning, a different number of frames will be retained within three different phases, and a different number of candidate ROIs (circle) will be retained within each frame, as shown in FIG. 4. In the timing constraint of the method model, two ROIs adjacent to each other in a chronological order must be close to each other at a spatial location. A dynamic programming algorithm in this method is: finding an ROI within a previous phase, so that the ROI is in the vicinity of a current ROI, and its score plus timing relationship score of the current ROI can reach a maximum value; and searching a local classifier, so that an appearance score of the current ROI is maximized. As shown in FIG. 4, a solid circle is an ROI selected by the dynamic programming algorithm.

After finding the optimal ROI, the method will adjust selection of the local classifier for each case, and increase, decrease, or maintain the number of local classifiers, thereby ensuring that the number of ROIs in each local classifier, i.e., a sub-class, is not too small, so as to achieve the purpose of reconfiguring the model structure. In this process, the goal of the method is to make the local classifier scores for each case selected as high as possible while making the ROIs as similar as possible between the cases where the same local classifier is selected. This method specifically maximizes the model score while maximizing the similarity measure of the two ROIs under the same local classifier, and makes the number of local classifiers as few as possible to prevent a situation that a local classifier is provided for a case during actual operation. Here, a Euclidean distance between two ROI features is specifically used as a measure of similarity therebetween, and a graph cut algorithm is used to solve the problem by converting into a graph label problem.

Figure 5:
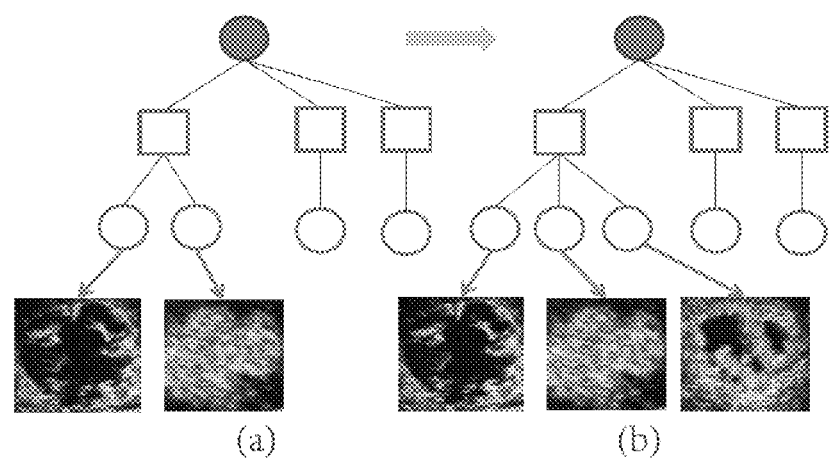
FIG. 5 is a reconfiguration diagram of a model structure.

After the problem is solved, the label of each node is the corresponding local classifier selected by the node or in the sample, and the ROI selected by the local classifier is the optimal ROI. At the same time, the number of local classifiers may also be determined, thereby completing the reconfiguration of the AND-OR model. As shown in FIG. 5, the model in (a) is reconfigured as the model in (b). In the first stage, a local classifier is added to represent a newly discovered lesion imaging pattern.

Figure 6:
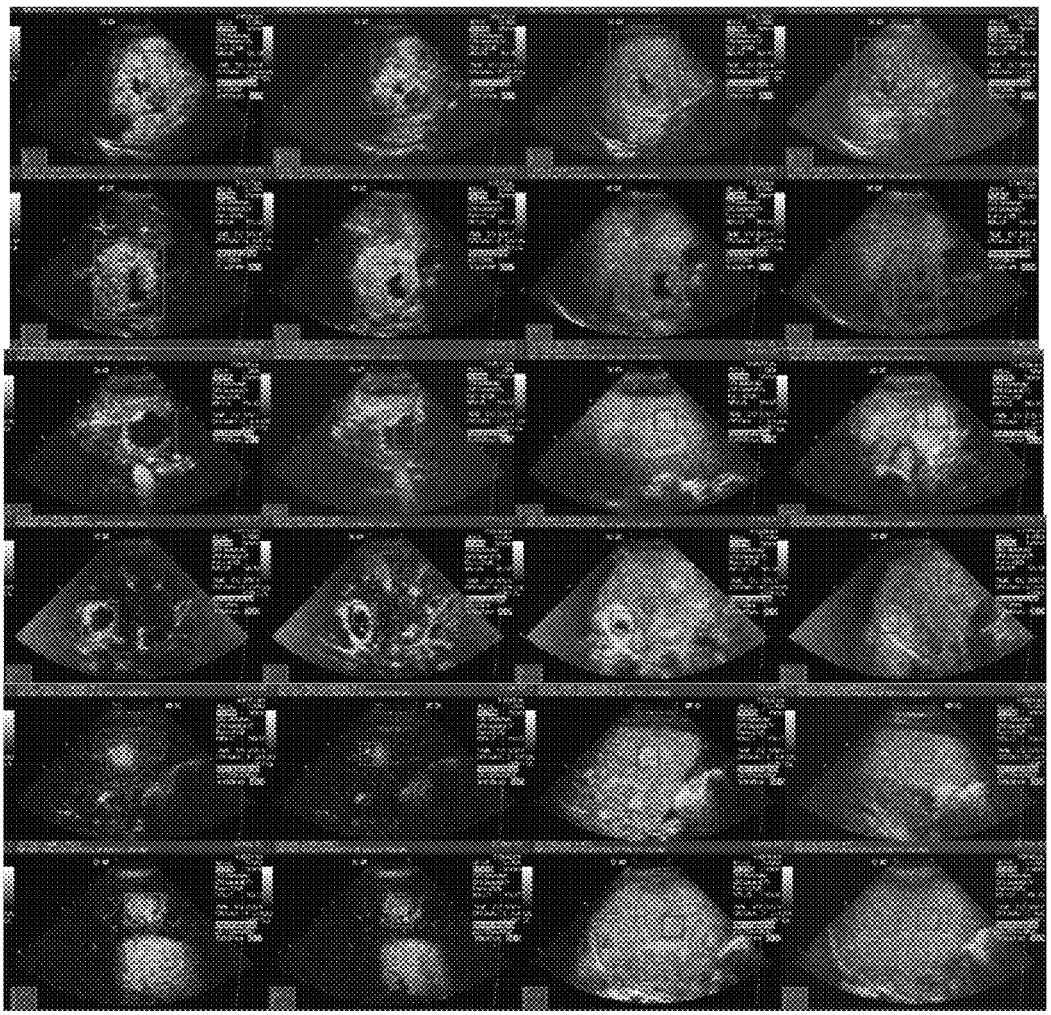
FIG. 6 is a partial result diagram of the method of the disclosure.

Finally, in S7 and S8, all possible classes are traversed, and the largest class is taken out as a recognition result, as shown in FIG. 6. At the same time, the found ROI is used as an analysis result of this method, and it can provide more information and reference for the aided diagnosis of a doctor.

The above-described embodiments of the disclosure do not limit the protection scope of the disclosure. Any modifications, equivalent replacements and improvements made within the spirit of the disclosure shall fall within the protection scope of the claims of the disclosure.

What is claimed is:
1. A method for automatically recognizing liver tumor types in ultrasound images, comprising:
   S1: using a model to represent a case, and using a local classifier to represent possible change forms of a lesion;
   S2: inputting ultrasound images of a group of cases and the type of liver cancer in each case as a training sample;
   S3: initializing the values of model parameters all to 0, or randomly initializing the values with a Gaussian probability distribution which has the expectation of zero;
   S4: based on the model parameters, in an ultrasound image video of a case, using a dynamic programming algorithm to search for an optimal Region of Interest (ROI) location, size, and time for each local classifier, so that when a model determines that the lesion class of the training sample is correct, a maximum score is obtained;
   S5: using a graph cut algorithm to determine a specific change form and ROI of the case;
   S6: based on the ROI determined in S5, using the training sample in S2 as an input, using a cutting-plane algorithm to train it, and using outputs of the algorithm as model parameters to obtain possible locations and sizes of lesions in the case and the number of local classifiers;
   S7: repeating S4 to S6 to acquire the lesion type of each case of a training sample data type, judging the correctness of the acquired lesion type, and when the number of judgment errors is fixed or the number of repetition steps reaches a preset value, obtaining training model parameters;
   S8: using the training model parameters acquired in S7 to determine an optimal ROI location, size, and time for all local classifiers in an ultrasound image video of a case to be detected, using a graph cut algorithm to determine a specific change form and ROI of the case to be detected, and using a model to obtain a probability score for a lesion according to the determined change form and ROI; and
   S9: repeating S2 to S8 for all lesion types in the case to be detected, and obtaining a probability score for one lesion by each repetition, a lesion type corresponding to the highest probability score being the lesion type of the case to be detected.

2. The method according to claim 1, wherein an ROI is respectively extracted for an input case ultrasound image at three phases namely an arterial phase, a portal phase and a delayed phase, the three ROIs being used to express FLLs;
   appearance features of an ROI interior, appearance features of an ROI boundary and appearance features of an ROI periphery are respectively extracted on the ROI interior, the ROI boundary and the ROI periphery of the ROI at each phase, and an average grayscale difference between the ROI interior and the ROI boundary and an average grayscale difference between the ROI interior and the ROI periphery are also acquired in the ROI at each phase; and
   when regional features of the ROI interior, the ROI boundary and the ROI periphery are extracted, the contrast, correlation, energy, and identity of a regional grayscale co-occurrence matrix are used as appearance features.

3. The method according to claim 2, wherein in S3, pruning is used first, and then an optimal ROI is searched by using a dynamic programming method, a specific process being as follows:
   a pruning process comprises time and space pruning;
   the time pruning is: calculating the grayscale feature of a grayscale co-occurrence focus in a certain frame in an ultrasound image video, and making a difference between vector frames to obtain a change value used to represent each frame; using a series of values obtained within a period of time to represent the degree of change of each frame within the period of time; arranging this series of values in a time sequence, and extracting the local maximum points to obtain a frame most dramatically changing within a period of time; selecting these frames corresponding to the local maximum points to obtain candidate frames of a lesion region; and in the remaining candidate frames, removing some unimportant regions based on experience;
   the space pruning is mainly achieved by using a priori of significance and location, comprising: calculating a saliency map of the entire image first, normalizing the saliency map, and averaging salient values in a region to obtain a salient value of the region, the priori of location being image-centered Gaussian distributions; and multiplying the values obtained from priori information of these two parts to obtain the probability that a certain region is an FLL region, and selecting a region of the probability is greater than the threshold as a candidate ROI;
   dynamic programming is used to search an ROI; after time and space pruning, a different number of frames will be retained within three different phases, and a different number of candidate ROIs will be retained within each frame; in the timing constraint, two ROIs adjacent to each other in a chronological order must be close to each other at a spatial location; the dynamic programming method is: finding an ROI within a previous phase, so that the ROI is in the vicinity of a current ROI, and its score plus timing relationship score of the current ROI can reach a maximum value; and searching a local classifier, so that an appearance score of the current ROI is maximized.

4. The method according to claim 3, wherein in S3, after searching for an optimal ROI, selection of the local classifier for the case will also be adjusted, the adjustment mode being: increasing, decreasing, or maintaining the number of local classifiers;

in this process, the goal is to maximize a local classifier score selected for each case while maximizing the similarity measure of two ROIs under the same local classifier.

5. The method according to claim 4, wherein a specific mode to achieve the above goal is: using a Euclidean distance between two ROI features as a measure of similarity therebetween, and using a graph cut algorithm to solve the problem by converting into a graph label problem.

* * * * *